United States Patent
Esplin

(10) Patent No.: US 9,949,455 B2
(45) Date of Patent: Apr. 24, 2018

(54) HYBRID VARIETY H1293

(71) Applicant: H.J. Heinz Company Brands LLC, Pittsburgh, PA (US)

(72) Inventor: David Esplin, Stockton, CA (US)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 164 days.

(21) Appl. No.: 14/935,347

(22) Filed: Nov. 6, 2015

(65) Prior Publication Data

US 2016/0057959 A1 Mar. 3, 2016

Related U.S. Application Data

(62) Division of application No. 14/098,417, filed on Dec. 5, 2013, now Pat. No. 9,439,375.

(60) Provisional application No. 61/735,830, filed on Dec. 11, 2012, provisional application No. 61/735,835, filed on Dec. 11, 2012.

(51) Int. Cl.
*A01H 5/08* (2006.01)
*A01H 1/00* (2006.01)
*A01H 1/02* (2006.01)
*C12N 15/00* (2006.01)

(52) U.S. Cl.
CPC .................. *A01H 5/08* (2013.01); *A01H 1/02* (2013.01)

(58) Field of Classification Search
None
See application file for complete search history.

(56) References Cited

U.S. PATENT DOCUMENTS

2011/0023174 A1* 1/2011 Bunn ................. A01H 5/08 800/268

* cited by examiner

*Primary Examiner* — Phoenix Bui
(74) *Attorney, Agent, or Firm* — Fitch, Even, Tabin & Flannery LLP

(57) ABSTRACT

Hybrid tomato variety 'H1293" is described. The 'H1293' tomato variety is a ground-culture hybrid tomato variety suitable for machine harvest, and is adaptable to the climactic conditions of regions such as California, USA, and Italy.

12 Claims, 2 Drawing Sheets
(2 of 2 Drawing Sheet(s) Filed in Color)

HYBRID VARIETY H1293

CROSS REFERENCE TO RELATED APPLICATIONS

This application is a divisional of U.S. application Ser. No. 14/098,417 filed on Dec. 5, 2013, which claims the benefit of U.S. Provisional Application No. 61/735,830, filed Dec. 11, 2012, and U.S. Provisional Application No. 61/735,835, filed Dec. 11, 2012, both of which are hereby incorporated by reference in their entirety.

FIELD

This invention relates to the field of plant breeding. In particular, this invention relates to new tomato, *Solanum lycopersicum*, varieties denominated 'H1292' and 'H1293'.

BACKGROUND

Breeding for improved tomato varieties involves providing genetics that give an advantage to the grower, processor, consumer, or other member of the supply chain. The improvement may be in the form of field performance, disease resistance, factory performance, or a fruit quality characteristic. For a tomato variety to be suitable to be grown for processing, the variety must have a concentrated fruit setting and maturity, firm fruit, and sufficient rot tolerance to allow early fruit to remain rot-free while later fruit continues to develop and ripen.

Most commercial processing tomato varieties are hybrids resulting from a cross pollination of two true-breeding, inbred parents. Through the use of true-breeding lines, a hybrid is produced that often displays characteristics of each parent, and often demonstrates characteristics that are superior to either parent alone, or that allow a hybrid to mask inadequacies of the individual parents.

Processing tomato varieties typically have a blocky to blocky-oval shape. However, an elongated shape that is referred to as a "pear" shape is preferred for some products and some market areas. Thus, a pear tomato variety (i.e., having a pear shape) can be valuable for certain products and markets.

SUMMARY

In order to meet this need, the present invention provides a new and improved process tomato varieties 'H1292' and 'H1293', which are pear tomato varieties with improved yield, brix, and disease resistances, as compared to the industry standard tomato variety 'H2601'. The varieties 'H1292' and 'H1293' are pear-shaped varieties with resistance to *Verticillium* race 1, *Fusarium* races 1 and 2, root knot nematode, and the tomato spotted wilt virus. The fruit of 'H1292' is firm with an average weight of 71.8 grams, and peels easily. The fruit of 'H1293' is also firm with an average weight of 72.1 grams, and peels easily. Additionally, 'H1292' and 'H1293' each has a level of fruit rot tolerance that makes the variety very adaptable for once-over machine harvest in regions such as California, Italy, and other countries with a Mediterranean climate.

The characteristics that determine the quality of tomato fruit used for processing are different from that of tomato fruit used for the fresh market. Processing characteristics are commonly tested on samples of tomato juice produced in a way that is well known in the art. For example, tomatoes are cooked in a microwave oven for several minutes, lost water is replaced, and the sample is poured into a pulper-finisher to remove skin and seeds and produce a uniform juice sample. Once cooled to room temperature, various tests can be run on the juice including juice Bostwick (a measure of gross viscosity or consistency), refractometer solids to measure soluble sugars and acids, pH, and color via Hunter a/b score. The Hunter a/b score is an international industry and USDA standard color measurement of tomato products that provides a representation of the color of the product in a single dimensionless unit. The "a" value represents color on the green to red dimension whereas "b" represents the blue to yellow dimension; a higher a/b ratio is associated with more red color and is often considered a superior product.

As used herein, tomato variety 'H1292', tomato plant 'H1292', tomato seed 'H1292', and 'H1292' all refer to the hybrid tomato variety 'H1292', and parts and seeds thereof, having ATCC Accession Number PTA-120873. As used herein, tomato variety 'H1293', tomato plant 'H1293', tomato seed 'H1293', and 'H1293' all refer to the hybrid tomato variety 'H1293', and parts and seeds thereof, having ATCC Accession Number PTA-120874.

Accordingly, in one embodiment, the present invention is directed to tomato seed designated as 'H1292' having ATCC Accession Number PTA-120873. In one embodiment, the present invention is directed to a tomato plant and parts isolated therefrom produced by growing 'H1292' tomato seed. In another embodiment, the present invention is directed to a tomato plant and parts isolated therefrom having all the physiological and morphological characteristics of a tomato plant produced by growing 'H1292' tomato seed having ATCC Accession Number PTA-120873. In still another embodiment, the present invention is directed to an $F_1$ hybrid tomato seed, plants grown from the seed, and leaves, ovules, pollen, fruit, cotyledons, embryos, meristems, anthers, roots, root tips, pistils, flowers, stems, calli, stalks, hypocotyls, and pericarps isolated therefrom having 'H1292' as a parent, wherein 'H1292' is grown from 'H1292' tomato seed having ATCC Accession Number PTA-120873.

Tomato plant parts include leaves, ovules, pollen, fruit, cotyledons, embryos, meristems, anthers, roots, root tips, pistils, flowers, stems, calli, stalks, hypocotyls, pericarps, and the like. In another embodiment, the present invention is further directed to tomato fruit, stems, leaves, parts of leaves, roots, root tips, pollen, ovules, and flowers isolated from 'H1292' tomato plants. In another embodiment, the present invention is further directed to tissue culture or cells derived from 'H1292' tomato plants.

In yet another embodiment, the present invention is further directed to a method of selecting tomato plants by a) growing 'H1292' tomato plants, where the 'H1292' plants are grown from tomato seed having ATCC Accession Number PTA-120873; and b) selecting a plant from step a). In another embodiment, the present invention is further directed to tomato plants, plant parts and seeds produced by the tomato plants, where the tomato plants are isolated by the selection method of the invention.

In another embodiment, the present invention is further directed to a method of breeding tomato plants by crossing a tomato plant with a plant grown from 'H1292' tomato seed having ATCC Accession Number PTA-120873. In still another embodiment, the present invention is further directed to tomato plants, tomato parts from the tomato plants, and seeds produced therefrom where the tomato plant is isolated by the breeding method of the invention.

In another embodiment, the present invention is directed to tomato seed designated as 'H1293' having ATCC Accession Number PTA-120874. In one embodiment, the present invention is directed to a tomato plant and parts isolated therefrom produced by growing 'H1293' tomato seed. In another embodiment, the present invention is directed to a tomato plant and parts isolated therefrom having all the physiological and morphological characteristics of a tomato plant produced by growing 'H1293' tomato seed having ATCC Accession Number PTA-120874. In still another embodiment, the present invention is directed to an $F_1$ hybrid tomato seed, plants grown from the seed, and leaves, ovules, pollen, fruit, cotyledons, embryos, meristems, anthers, roots, root tips, pistils, flowers, stems, calli, stalks, hypocotyls, and pericarps isolated therefrom having 'H1293' as a parent, wherein 'H1293' is grown from 'H1293' tomato seed having ATCC Accession Number PTA-120874.

Tomato plant parts include leaves, ovules, pollen, fruit, cotyledons, embryos, meristems, anthers, roots, root tips, pistils, flowers, stems, calli, stalks, hypocotyls, pericarps, and the like. In another embodiment, the present invention is further directed to tomato fruit, stems, leaves, parts of leaves, roots, root tips, pollen, ovules, and flowers isolated from 'H1293' tomato plants. In another embodiment, the present invention is further directed to tissue culture or cells derived from 'H1293' tomato plants.

In yet another embodiment, the present invention is further directed to a method of selecting tomato plants by a) growing 'H1293' tomato plants, where the 'H1293' plants are grown from tomato seed having ATCC Accession Number PTA-120874; and b) selecting a plant from step a). In another embodiment, the present invention is further directed to tomato plants, plant parts and seeds produced by the tomato plants, where the tomato plants are isolated by the selection method of the invention.

In another embodiment, the present invention is further directed to a method of breeding tomato plants by crossing a tomato plant with a plant grown from 'H1293' tomato seed having ATCC Accession Number PTA-120874. In still another embodiment, the present invention is further directed to tomato plants, tomato parts from the tomato plants, and seeds produced therefrom where the tomato plant is isolated by the breeding method of the invention.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION

Described herein are new and distinct tomato varieties named 'H1292' and 'H1293' that were developed to provide ground-culture hybrid tomato varieties (i.e., not grown on stakes) that are suitable for machine harvest, and is adaptable to the climactic conditions of regions such as California, USA, and Italy.

Plants of tomato varieties 'H1292' and 'H1293' are resistant to Verticillium wilt race 1, Fusarium wilt races 1 and 2, root knot nematode, and tomato spotted wilt virus. Additionally, plants of the tomato varieties 'H1292' and 'H1293' are dark green in color and medium in size compared to other tomato varieties of the same market class. Fruit from the tomato variety 'H1292' is firm and peels easily. Moreover, the tomato varieties 'H1292' and 'H1293' are adapted to culture in regions such as California, USA, and Italy.

Stability of the tomato varieties 'H1292' and 'H1293'

The tomato varieties 'H1292' and 'H1293' are uniform and stable within commercially acceptable limits. As is true with other tomato varieties, a small percentage of variants can occur within commercially acceptable limits for almost any characteristic during the course of repeated multiplication. However no variants were observed during the two years in which the variety was observed to be uniform and stable.

Figure 1:
FIG. 1 illustrates fruit from the tomato variety 'H1292'.

Characterization of the 'H1292' tomato variety
Seedling
Anthocyanin in hypocotyl of 2-15 cm seedling: Present
Habit of 3-4 week old seedling: Normal
Mature Plant
Average height (in cm): 40 cm (from ground culture, i.e., non-staked)
Growth: Determinate
Form: Normal
Size of canopy (compared to others of similar type): Medium
Habit: Sprawling (e.g., decumbent)
Stem
Average length (in cm): 69 cm
Branching: Profuse (e.g., 'UC 82')
Branching at cotyledonary or first leafy node: Absent
Number of nodes below first inflorescence: 7-10
Number of nodes between early (1st-2nd, 2nd-3rd) inflorescences: 1-2
Number of nodes between later developing inflorescences: 1-2
Pubescence on younger stems: Sparsely hairy (scattered long hairs)
Leaf (Mature Leaf Beneath the 3rd Inflorescence)
Type: Tomato
Please describe morphology of mature leaf: Compound with major and minor leaflets (FIG. 1)
Average length and width (in cm): 31.7×23.2 cm
Margins of major leaflets: Deeply toothed or cut, sps. Toward base
Marginal rolling or wiltiness: Moderate
Onset of leaflet rolling: Mid-season
Surface of major leaflets: Rugose (bumpy or veiny)
Pubescence: Normal
Inflorescence (Make Observations on 3rd Inflorescence)
Type: Simple
Average number of flowers in inflorescence: 5.7
Leafy or "running" inflorescences: Absent
Flower
Calyx: Normal, lobes awl-shaped
Calyx-lobes: Shorter than corolla
Corolla color: Yellow
Style pubescence: Absent
Anthers: All fused into tube
Fasciation (1st flower of 2nd or 3rd inflorescence): Absent
Fruit (3rd Fruit of 2nd or 3rd Cluster)
Describe the typical fruit shape: Long (FIG. 1)
Describe the Shape of transverse section: Round
Describe the shape of stem end: Flat
Describe the shape of blossom end: Tapered
Describe the shape of pistil scar: Dot
Abscission layer: Absent (jointless)
Point of detachment of fruit at harvest: At calyx attachment
Provide the average length (in mm) of dedicel (from joint to calyx attachment): 24.2 mm Provide the average length (in mm) of mature fruit (stem axis): 74.5 mm
Provide the average diameter (in mm) of fruit at widest point: 40.9 mm
Provide the average weight (in g) of mature fruit: 71.8 grams
Number of locules: Two
Fruit surface: Smooth
Fruit base color (mature-green stage): Light green (e.g., 'Lanai', 'VF 145-F5')
Fruit pattern (mature-green stage): Uniform green
Fruit color, full-ripe: Red
Flesh color full-ripe: Red/Crimson
Flesh color: Uniform
Locular gel color of table-ripe fruit: Red
Ripening: Uniform
Ripening: Uniformly
Stem scar size: Small (e.g., 'Roma')
Core: Coreless (absent or smaller than 6×6 MM)
Epidermis color: Yellow
Epidermis: Easy-peel
Epidermis texture: Average
Describe the thickness of the pericarp: Medium
Anthocyanin in hypocotyl of 2-15 cm seedling: Present
Habit of 3-4 week old seedling: Normal
Disease and Pest Reaction
Disease and Pest Reaction: Resistant to *Verticillium* wilt, race 1, *Fusarium* races 1 and 2, root knot nematode, *Alternaria* stem canker, *Stemphylium*, *Pseudomonas syringae* pv tomato race 0, and Tomato spotted wilt virus.
Chemistry and Composition of Full-Ripe Fruits

TABLE 1

|  | Variety 'H1292' | Check Variety 1 'Docet' | Check Variety 2 'H2601' |
| --- | --- | --- | --- |
| Soluble solids as ° Brix | 5.68 | 5.10 | 5.17 |
| Juice Bostwick | 12.2 | 12.7 | 13.5 |

Figure 2:
FIG. 2 illustrates fruit from the tomato variety 'H1293'.

Fruiting season: Very concentrated (e.g., 'TIC 82')
Relative maturity in areas tested: Medium early
Adaptation
Culture: Field
Principle use(s): Whole-pack canning; and concentrated products
Machine harvest: Adapted
Regions to which adaptation has been demonstrated: California: Sacramento and Upper San Joaquin Valley; and California: Southern San Joaquin Valley and deserts
Characterization of the 'H1293' tomato variety
Seedling
Anthocyanin in hypocotyl of 2-15 cm seedling: Present
Habit of 3-4 week old seedling: Normal
Mature Plant
Average height (in cm): 41 cm (from ground culture, i.e., non-staked)
Growth: Determinate
Form: Normal
Size of canopy (compared to others of similar type): Medium
Habit: Sprawling (e.g., decumbent)
Stem
Average length (in cm): 53 cm
Branching: Profuse (e.g., 'UC 82')
Branching at cotyledonary or first leafy node: Absent
Number of nodes below first inflorescence: 7-10
Number of nodes between early (1st-2nd, 2nd-3rd) inflorescences: 1-2
Number of nodes between later developing inflorescences: 1-2
Pubescence on younger stems: Sparsely hairy (scattered long hairs)
Leaf (Mature Leaf Beneath the 3rd Inflorescence)
Type: Tomato
Please describe morphology of mature leaf: Compound with major and minor leaflets (FIG. 2)
Average length and width (in cm): 29.3×26.7 cm
Margins of major leaflets: Shallowly toothed or scalloped
Marginal rolling or wiltiness: Moderate
Onset of leaflet rolling: Mid-season
Surface of major leaflets: Rugose (bumpy or veiny)
Pubescence: Normal
Inflorescence (Make Observations on 3rd Inflorescence)
Type: Simple
Average number of flowers in inflorescence: 5.0
Leafy or "running" inflorescences: Absent
Flower
Calyx: Normal, lobes awl-shaped
Calyx-lobes: Shorter the corolla
Corolla color: Yellow
Style pubescence: Absent
Anthers: All fused into tube
Fasciation (1st flower of 2nd or 3rd inflorescence): Absent
Fruit (3rd Fruit of 2nd or 3rd Cluster)
Describe the typical fruit shape: Long (FIG. 2)
Describe the Shape of transverse section: Round
Describe the shape of stem end: Flat
Describe the shape of blossom end: Tapered
Describe the shape of pistil scar: Dot
Abscission layer: Absent (jointless)
Point of detachment of fruit at harvest: At calyx attachment
Provide the average length (in mm) of dedicel (from joint to calyx attachment): 23.9 mm
Provide the average length (in mm) of mature fruit (stem axis): 75.8 mm
Provide the average diameter (in mm) of fruit at widest point: 41.5 mm
Provide the average weight (in g) of mature fruit: 72.1 grams
Number of locules: Two
Fruit surface: Smooth
Fruit base color (mature-green stage): Light green (e.g., 'Lanai', 'VF 145-F5')
Fruit pattern (mature-green stage): Uniform green
Fruit color, full-ripe: Red
Flesh color full-ripe: Red/Crimson
Flesh color: Uniform
Locular gel color of table-ripe fruit: Red
Ripening: Uniform
Ripening: Uniformly
Stem scar size: Small (e.g., 'Roma')
Core: Coreless (absent or smaller than 6×6 MM)
Epidermis color: Yellow
Epidermis: Easy-peel
Epidermis texture: Average
Describe the thickness of the pericarp: Medium
Anthocyanin in hypocotyl of 2-15 mc seedling: Present
Habit of 3-4 week old seedling: Normal
Disease and Pest Reaction
Disease and Pest Reaction: Resistant to *Verticillium* wilt, race 1, *Fusarium* races 1 and 2, root knot nematode, *Alternaria* stem canker, *Stemphylium*, *Pseudomonas syringae* pv tomato race 0, and Tomato spotted wilt virus.
Chemistry and Composition of Full-Ripe Fruits

TABLE 2

|  | Variety 'H1293' | Check Variety 'Docet' | Check Variety 'H2601' |
|---|---|---|---|
| Soluble solids as ° Brix | 5.71 | 5.10 | 5.17 |
| Juice Bostwick | 12.2 | 12.7 | 13.5 |

Fruiting season: Very concentrated (e.g., 'UC 82')
Relative maturity in areas tested: Medium early
Adaptation
Culture: Field
Principle use(s): Whole-pack canning; and concentrated products
Machine harvest: Adapted
Regions to which adaptation has been demonstrated: California: Sacramento and Upper San Joaquin Valley; and California: Southern San Joaquin Valley and deserts Further Embodiments Additional methods include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present invention relates a method for producing an inbred tomato variety by: planting seed of the tomato variety 'H1292' or 'H1293'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'H1292' or 'H1293'. Tomato plants capable of expressing substantially all of the physiological and morphological characteristics of the parental inbred lines of tomato varieties 'H1292' and 'H1293' include tomato plants obtained by chasing selfs from seed of tomato varieties 'H1292' and 'H1293'.

One of ordinary skill in the art will recognize that once a breeder has obtained inbred tomato plants by chasing selfs from seed of tomato variety 'H1292' or 'H1293', the breeder can then produce new inbred plants such as by sib-pollinating, or by crossing one of the identified inbred tomato plant with a plant of the tomato variety 'H1292' or 'H1293'.

DEPOSIT INFORMATION

A deposit of the tomato variety 'H1292' is maintained by HeinzSeed Company, having an address at 6755 C. E. Dixon, Stockton, Calif. 95206, United States of America. A deposit of the tomato variety 'H1293' is maintained by HeinzSeed Company, having an address at 6755 C. E. Dixon, Stockton, Calif. 95206, United States of America. Access to these deposits will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the varieties 'H1292' and 'H1293' will be irrevocably removed by affording access to a deposit of at least 2,500 seeds of the same varieties with the American Type Culture Collection, (ATCC), ATCC Patent Depository, 10801 University Boulevard, Manassas, Va., 20110, USA.

At least 2500 seeds of tomato variety 'H1292' were deposited on Jan. 21, 2014 according to the Budapest Treaty in the American Type Culture Collection (ATCC), ATCC Patent Depository, 10801 University Boulevard, Manassas, Va., 20110, USA. The deposit has been assigned ATCC number PTA-120873. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed for the enforceable life of the patent.

At least 2500 seeds of tomato variety 'H1293' were deposited on Jan. 21, 2014 according to the Budapest Treaty in the American Type Culture Collection (ATCC), ATCC Patent Depository, 10801 University Boulevard, Manassas, Va., 20110, USA. The deposit has been assigned ATCC number PTA-120874. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed for the enforceable life of the patent.

Each of the deposits will be maintained in the ATCC depository, which is a public depository, for a period of 30 years, or 5 years after the most recent request, or for the effective life of the patent, whichever is longer, and will be replaced if a deposit becomes nonviable during that period.

The invention claimed is:

1. Tomato seed designated as 'H1293', representative sample of seed having been deposited under ATCC Accession Number PTA-120874.

2. A plant produced by growing the seed of claim 1.

3. A plant part from the plant of claim 2.

4. The plant part of claim 3, wherein said part is selected from the group consisting of leaves, ovules, pollen, tomato fruit, cotyledons, meristems, anthers, roots, root tips, pistils, flowers, stems, calli, stalks, hypocotyls, and pericarps.

5. A tomato plant having all the physiological and morphological characteristics of the tomato plant of claim 2.

6. A plant part from the plant of claim 5.

7. The plant part of claim 6, wherein said part is selected from the group consisting of leaves, ovules, pollen, tomato fruit, cotyledons, meristems, anthers, roots, root tips, pistils, flowers, stems, calli, stalks, hypocotyls, and pericarps.

8. Pollen or an ovule of the plant of claim 2.

9. A tissue culture of the plant of claim 2.

10. A method of making tomato seeds comprised of crossing the plant of claim 2 with another tomato plant and harvesting seed therefrom.

11. The plant part of claim 4, wherein said part is a tomato fruit.

12. The plant part of claim 7, wherein said part is a tomato fruit.

* * * * *